United States Patent
Sasaki et al.

(10) Patent No.: US 8,473,058 B2
(45) Date of Patent: *Jun. 25, 2013

(54) APNEA PREVENTING STIMULATION APPARATUS

(75) Inventors: Mitsuru Sasaki, Fukushima (JP); Tatsuyuki Kobayashi, Niigata (JP)

(73) Assignees: Mitsuru Sasaki, Fukushima (JP); Techno Link Co., Ltd., Niigata (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/463,374

(22) Filed: May 3, 2012

(65) Prior Publication Data

US 2012/0232611 A1    Sep. 13, 2012

Related U.S. Application Data

(63) Continuation-in-part of application No. 11/719,939, filed as application No. PCT/JP2004/017337 on Nov. 22, 2004, now abandoned.

(51) Int. Cl.
*A61N 1/00* (2006.01)

(52) U.S. Cl.
USPC ............................................... 607/42

(58) Field of Classification Search
USPC ................................................ 607/42, 72
See application file for complete search history.

(56) References Cited

U.S. PATENT DOCUMENTS

| | | | | |
|---|---|---|---|---|
| 4,750,482 | A | * | 6/1988 | Sieverding .................. 604/317 |
| 5,190,053 | A | * | 3/1993 | Meer ............................ 607/134 |
| 6,526,319 | B2 | * | 2/2003 | Kobayashi ..................... 607/72 |
| 7,191,014 | B2 | * | 3/2007 | Kobayashi et al. ............ 607/72 |
| 2005/0085866 | A1 | * | 4/2005 | Tehrani ........................... 607/42 |

FOREIGN PATENT DOCUMENTS

| | | |
|---|---|---|
| JP | 03-023870 A | 1/1991 |
| JP | 6-508288 A | 9/1994 |
| JP | 8-224317 A | 9/1996 |
| JP | 2794196 B2 | 6/1998 |
| JP | 2001-259048 A | 9/2001 |
| JP | 2003-190303 A | 7/2003 |
| WO | 93/18820 A1 | 9/1993 |

* cited by examiner

*Primary Examiner* — Christopher D Koharski
*Assistant Examiner* — Nadia Ahmad
(74) *Attorney, Agent, or Firm* — McDermott Will & Emery LLP

(57) ABSTRACT

An apnea preventing stimulation apparatus having a conductive unit is attached to a mental region of a patient and electric pulses flow from the conductive unit to the mental region of the patient to thereby apply stimuli thereto. A formula is utilized to increase a rate of an output level of the amplitude in an electric pulse until a first time width elapses. Consequently, immediately after outputting stimulation signals, the amplitude of the electric pulse groups does not abruptly increase, thus enabling the patient to be hardly affected by the stimulation signals. Until just before the time reaches the end of a time width after the output start of the stimulation signal, the rate of the output level of the amplitude in the electric pulse groups does not reach 1, permitting the emotional strain on the patient to be eased.

12 Claims, 9 Drawing Sheets

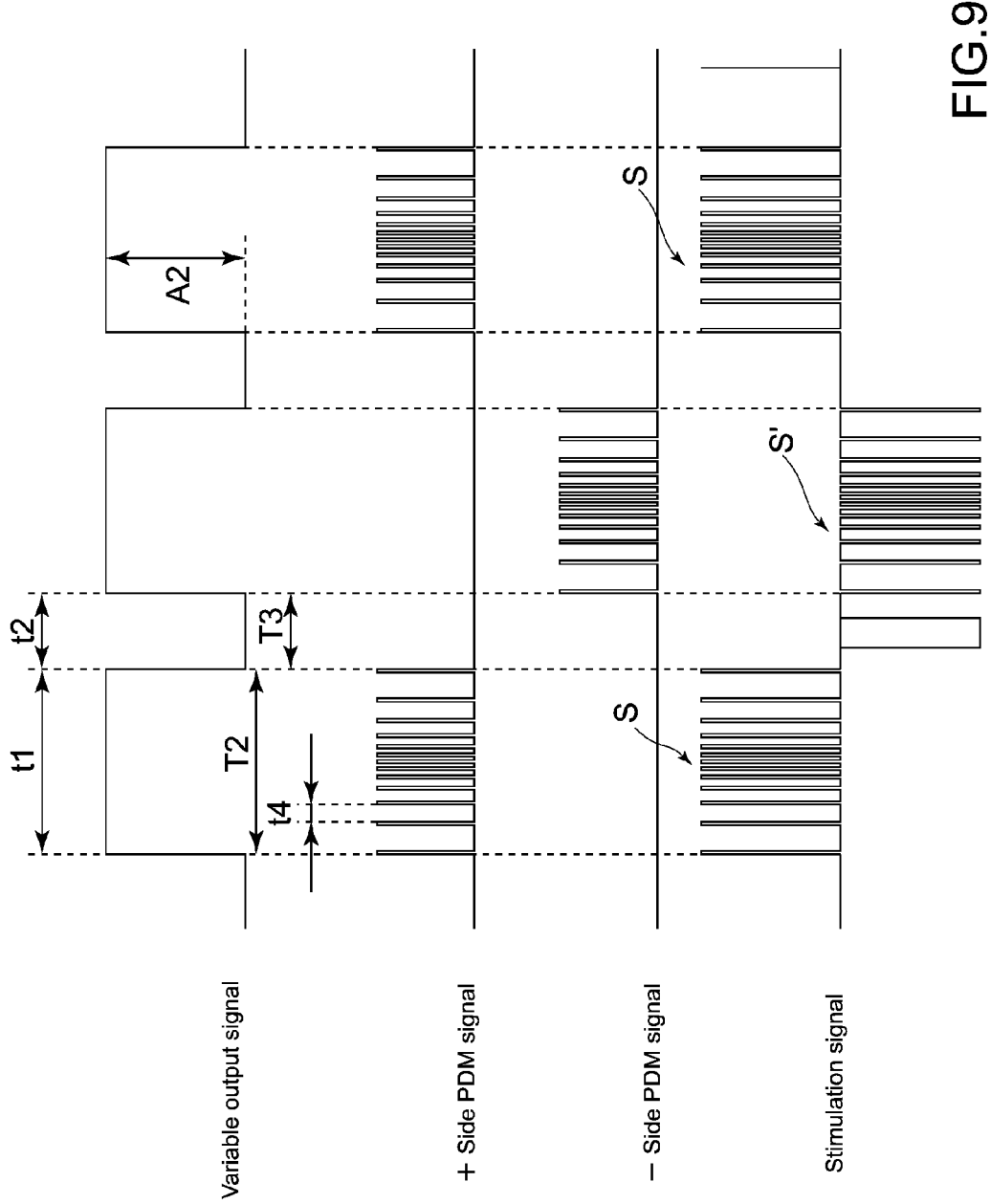

APNEA PREVENTING STIMULATION APPARATUS

CROSS REFERENCE TO RELATED APPLICATIONS

This application is a continuation-in-part application of U.S. application Ser. No. 11/719,939 which was the U.S. national phase application under 35 U.S.C. §371 of international patent application No. PCT/JP2004/017337 filed on Nov. 22, 2004. This parent application is expressly incorporated by reference herein in its entirety.

TECHNICAL FIELD

The present invention relates to an apnea preventing stimulation apparatus for preventing the occurrence of trouble which results from abnormality in the respiratory function in one's sleep.

BACKGROUND ART

Many studies have been reported on a so-called sleep-apnea syndrome, i.e. apnea which is accompanied by the suspension of breathing, for example, for 10 seconds or more in one's sleep at night.

If breathing comes to stop a few dozen times to hundreds of times during sleep, lack of oxygen in the body of a patient reaches a serious level, thus displaying symptoms such as "insomnia" and "choking" during sleep. As a result, the patient falls into a state of lack of sleep.

Accordingly, the patient gets sleepy in the daytime, leading to low concentration and a low energy level, or to dozing while working, which can cause serious accidents, such as those caused by drowsy driving.

Moreover, lack of oxygen will place undue stress on circulation organs, leading to the increased incidence of abnormal cardiac rhythm, high blood pressure, heart failure and diabetes. Thus, the respiratory abnormality in one's sleep is a clinically important subject, and it is necessary to take measures for preventing the occurrence of the above-mentioned disorders.

The sleep-apnea syndrome is classified into a so-called central type caused by an abnormality in the respiratory center, an obstructive type by an upper airway obstruction, and a mixed type by a combination thereof.

As for the obstructive type that often causes the sleep-apnea syndrome, there have been conventionally known methods of treatment for opening the closed upper airway, by, for example, putting a mouthpiece into a patient's mouth to fix a lower jaw in such a manner protruding forward, or by letting a patient put on a plastic nasal cavity mask at the time of sleeping, and then pumping air from a pumping installation connected with the nasal cavity mask through a hose.

According to the former method, however, since the patient cannot take breaths through the mouth with the mouthpiece put therein, it can not be used when he/she has nasal congestion. According to the latter method, the patient must put on a nasal cavity mask for feeding air to his/her face, and thus there is a possibility that the patient may experience discomfort during sleep.

To address the foregoing problems, Japanese Registered Patent Publication No. 2794196 proposes an apnea preventive stimulating device in which a respiratory condition of a patient is detected by a respiration detection device such as a thermistor, and if the respiration detection device determines that the patient is in a respiratory standstill, then stimulating signals comprising electric pulses of a frequency of 40 to 150 Hz, a peak value of 1 to 50 volts and rise-up time constant of 0.2 seconds or more, are applied to his/her genioglossus muscle, which is one of the dilator muscles of the closed upper airway.

The apnea preventive stimulating device of the foregoing structure is advantageous in that since it applies stimulating signals to genioglossus muscle without using an air pressure, it is not necessary to put on a nasal cavity mask covering a substantial area on a face, and that the upper airway can be recovered from obstruction promptly, irrespective of whether the patient has nasal congestion or not.

According to the device, however, the stimulation signals are only applied when the patient is determined to be in the respiratory standstill after detecting his/her respiratory condition, and thus two or more thermistors need to be attached to the neighborhood of both nostrils or a mouth of the patient. Besides, the patient is liable to be wakened due to the stimulation signals being applied synchronously with the respiratory standstill of the patient.

SUMMARY OF THE INVENTION

It is, therefore, an object of the present invention to provide an apnea preventing stimulation apparatus which enables stimulation signals to be effectively applied to a mental region of a patient while disturbing his/her sleep as least as possible, without the need of any respiratory condition monitoring system.

A first aspect of the present invention is an apnea preventing stimulation apparatus including a conductor unit to allow electric pulses to flow from the conductor unit through a mental region of the patient, the apparatus including:

a first operation device for starting output of the stimulation signals, and a stimulus generating device for outputting stimulation signals to the conductor unit as soon as the start of output thereof is directed regardless of whether the patient is in a sleep apnea or not at that moment, the stimulation signal repeating, for a given length of time, alternately a conduction period during which electric pulse groups comprising a plurality of the electric pulses are generated and a pause period during which no such electric pulse groups are generated, wherein the stimulus generating device outputs the stimulation signals in such a manner that amplitude of the electric pulse increases gradually from start of output of the stimulation signals until the lapse of a first time width, which is defined as a time width from the start of output until the gradually increasing amplitude thereof is finally stabilized, so that for a short period from the output start of the stimulation signals, the amplitude of the electric pulse is small and then increases as time goes by for the patient to fall asleep, wherein when the first time width is defined as T and a time from the output start of the stimulation signals is defined as t, a rate of an output level R of the amplitude in the electric pulse until the lapse of the first time width T is increased according to the following formula:

$$R=1-((1-t/T))^N, \text{ where } 1.5 \leq N \leq 3.$$

The apnea preventing stimulation apparatus according to another aspect of the invention further includes a second operation device for varying the amplitude of the electric pulse.

The apnea preventing stimulation apparatus according to still another aspect of the invention further includes a third operation device for varying the conduction period.

The apnea preventing stimulation apparatus according to still another aspect of the invention further includes a fourth operation device for varying the pause period.

The apnea preventing stimulation apparatus according to yet another aspect of the invention further includes a fifth operation device for stopping the output of the stimulation signals.

The apnea preventing stimulation apparatus according to yet another aspect of the invention further includes a sixth operation device for varying the first time width.

According to the apnea preventing stimulation apparatus according to a further aspect, the stimulus generating device outputs the stimulation signals in which the time widths of a plurality of the electric pulses constituting the electric pulse are varied during the output of the electric pulse groups.

According to the apnea preventing stimulation apparatus according to a still further aspect of the invention, the stimulus generating device generates alternately the positive and negative electric pulse groups each having a second time width during the conduction period, and outputs the stimulation signals in such a way that the time width of each electric pulse gradually widens until half the second time width elapses from the rising edge of the electric pulse group and then gradually narrows as coming closer to the falling edge of the electric pulse group.

According to the apnea preventing stimulation apparatus according to a still further aspect of the invention, the stimulus generating device outputs the stimulation signals in which the density of a plurality of the electric pulses constituting the electric pulse groups varies during the output of the electric pulse groups.

According to the apnea preventing stimulation apparatus according to a yet further aspect of the invention, the stimulus generating device outputs alternately the positive and negative electric pulse groups each having a second time width during the conduction period, and outputs the stimulation signals in such a way that an electric pulse density gradually increases until half the second time width elapses from the rising edge of the electric pulse group and then gradually narrows as coming closer to the falling edge of the electric pulse group.

According to the apnea preventing stimulation apparatus according to still another aspect of the invention, the conductive unit comprises a couple of electrodes to which the stimulation signals are applied, and an adhesive sheet member that holds the electrodes and is detachably attached to the mental region of the patient.

According to the apnea preventing stimulation apparatus according to yet another aspect of the invention, the sheet member arranges the electrodes so that the couple of the electrodes are juxtaposed to each other in a front-back direction of a mental region of the patient.

Thus, the stimulation signal which repeats the conduction period serving to generate the electric pulse groups and the pause period serving to generate no electric pulse group is effectively applied from the stimulus generating device to the mental region of the patient through the conductor unit, and thus the obstruction of the upper airway is promptly removed without the need to monitor a respiratory condition of the patient. Moreover, since the stimulation signal which repeats the conduction period and pause period of the above-mentioned electric pulse group is applied to the mental region of the patient regardless of whether the patient is in a sleep apnea or not, the patient is less likely to be awakened by the stimulation signal and thus he/she can get sufficient sleep. Accordingly, even if the respiratory state is not monitored, the stimulation signal can be effectively applied to the mental region of the patient, with minimal disturbance in his/her sleep.

Furthermore, by operating the first operation device in synchronization with a bedtime, it is possible to output the stimulation signal to the conductor unit from that time. And since the amplitude of the electric pulse is small at the time of starting to output the stimulation signal, the influence on the sleep from the stimulation signal can be reduced to minimum. Moreover, since the amplitude of the electric pulse gradually increases as the patient falls asleep, it is possible to give the patient such stimulation signals that enable avoiding of sleep apnea reliably.

Moreover, by utilizing the above formula to define the rate of output level R of the amplitude in an electric pulse during an elapse of the first time width, immediately after starting output of the stimulation signals, the amplitude of the electric pulse does not increase abruptly for the patient to be less affected by the stimulation signals. Then, until just before the time elapsing from the start of output of the stimulation signals reaches the first time width, the rate of output level R of the amplitude in the electric pulse does not become 1, thus enabling an emotional strain on the patient to be eased.

Further, the amplitude of the electric pulse generated during the conduction period can be varied by the second operation device. Accordingly, the electric pulse of optimal amplitude can be given to any patients.

Still further, the conduction period to generate the electric pulse group can be varied arbitrarily by the second operation device. Accordingly, the stimulation signal with an optimal conduction period can be given to any patients.

Furthermore, the pause period to generate no electric pulse group can be varied arbitrarily by the fourth operation device. Accordingly, the stimulation signal with optimal pause period can be given to any patients.

Moreover, when the patient is awakened for some reasons during the sleep, the medical treatment can be temporarily stopped by operating the fifth operation device to stop the output of the stimulation signal. In this way, providing the first and fifth operation device enables the patient to choose whether to start or to stop outputting the stimulation signals on his/her free will.

Moreover, since the time taken to fall asleep varies from person to person, the variable control of the first time width by the sixth operation device enables the stimulation signals to be given to any patients in order to allow the patient to avoid sleep apnea reliably.

Furthermore, since the stimulus generating device performs arbitrarily variable control of the time width of the individual electric pulse constituting the electric pulse group, the waveform of the low frequency applied into the body of a patient can be distorted into a desirable state according to the increase or decrease of the time width of the electric pulse.

Still moreover, when the stimulus generating device outputs the stimulation signals, the electric pulse group comprising two or more high frequency signal components (electric pulses) is repeatedly applied from the conductor unit to a patent as a stimulation signal, yet the waveform of each electric pulse group is distorted by the capacitive element of the patient and thus the stimulation signal takes the waveform approximated to a low frequency sinusoidal wave. Accordingly, it is possible to avoid an apneic state effectively with an extremely soft feeling of stimulation as compared with a feeling caused by the application of rectangular waves of the same current and frequency.

Furthermore, since the stimulus generating device performs arbitrarily variable control of the density of electric pulses which constitute each electric pulse group, the low frequency waveform can be distorted into a desirable state according to the density of the electric pulses in the body of a patient. Besides, the time width of each electric pulse is made constant and a pause period between the electric pulses is varied by the stimulus generating device during the output of the electric pulse groups, resulting in the absence of comparatively large-time width electric pulses, which in turn device that the charge current to a patient's equivalent capacitance is supplied little by little, so that the amount of charge rises gently, enabling a more physically soft feeling of stimulation to be applied.

Moreover, when the stimulus generating device outputs a stimulation signal, the waveform of each electric pulse group is distorted in the body of a patient, and thus the stimulation signal can take such a waveform as the high frequency electric pulses are superimposed on a signal approximated to a low frequency sinusoidal wave. Accordingly, it is possible to avoid an apneic state effectively, with an extremely soft feeling of stimulation as compared with a feeling caused by the application of rectangular wave of the same current and frequency.

Moreover, the conductor unit including the electrodes can be attached to a desired position only by sticking the sheet member to the patient's mental region, thus enabling an operator to save the trouble of attaching a pair of electrodes, one by one.

Still moreover, since a pair of electrodes can be arranged on the front-back direction of the mental region only by sticking the sheet member on the patient's mental region, the influence of stimulation signals on the brain waves can be controlled to the minimum, enabling it to be discerned correctly whether the patient is in an asleep condition or not.

BRIEF DESCRIPTION OF THE DRAWINGS

FIG. 9 is an enlarged waveform diagram of the stimulating signal showing waveforms in respective parts thereof after the lapse of the first time width in accordance with the second embodiment of the invention.

DETAILED DESCRIPTION OF THE INVENTION

Next is a description of an apnea preventing stimulation apparatus in accordance with preferred embodiments of the present invention with reference to the accompanying drawings.

Figure 1:
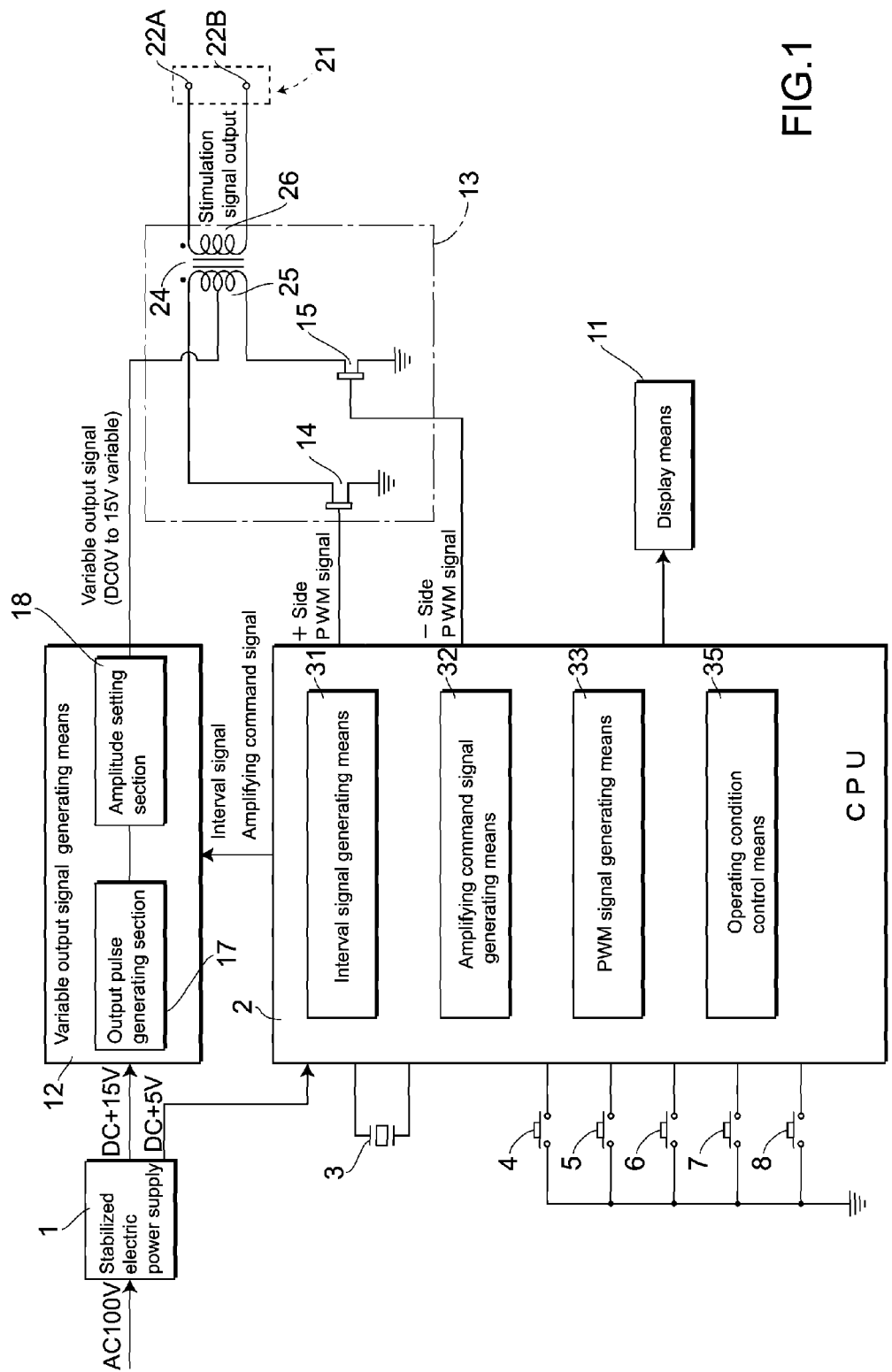
FIG. 1 is a block diagram showing an overall structure of an apnea preventing stimulation apparatus in accordance with a first embodiment of the invention.

FIG. 1 is a block diagram showing an overall configuration of an apparatus in accordance with a first embodiment of the present invention. In the drawing, FIG. 1 designates a stabilized power supply for converting an AC input into a stabilized DC output. In the present embodiment, AC 100V is converted into DC+15V and DC+5V. Numeral 2 designates a CPU (Central Processing Unit) serving as a control device actuated by the DC+5V from the stabilized power supply 1 and reference clock signals from a crystal oscillator 3. As is well known, the CPU 2 is integrated with an input/output device, a memory device, an arithmetic processing device, etc. so that a stimulating current of a predetermined pattern may be applied to a human body as a living body (not shown) according to a control sequence memorized in the memory device.

To input ports of the CPU 2 are connected an operation device comprising a plurality of button switches 4 to 8. On the other hand, to output ports thereof is connected a display device 11 comprising LEDs or LCDs, for example. Furthermore, to the output ports of the CPU 2 are connected respective gates of two FETs 14, 15 constituting a stimulus generating device 13 and a variable output signal generating device 12 for generating variable output signals to determine the amplitude, on time and off time of individual electric pulse groups in the stimulating signals.

The variable output signal generating device 12 is powered by the DC voltage of DC+15V from the stabilized power supply 1, and comprises an output pulse generating section 17 which generates an output pulse in response to an interval signal for serving as a first control signal from CPU2, and an amplitude setting section 18 which determines the amplitude of the output pulse in response to an amplifying command signal for serving as a second control signal from CPU2, so that variable output signals of rectangular waveforms whose amplitude are modulated in a range of from DC 0V to DC+15V is supplied to the stimulus generating device 13

The stimulus generating device 13 outputs the stimulation signals across a pair of output terminals 22A, 22B serving as the electrodes of the conductor unit 21. The stimulation signals repeat, at the second-time-scale regular intervals, the conduction period in which the electric pulse groups are continuously or intermittently generated and the pause period in which no electric pulse groups are generated, by device of the variable output signals outputted from the variable output signal generating device 12 and the electric pulse generating signals. i.e., PWM (Pulse Width modulation) signals outputted from CPU 2 to each of FETs 14 and 15. More specifically, the stimulus generating device 13 in the present embodiment comprises a transformer 24 of which the primary and secondary sides are isolated from each other in addition to the FETs 9 and 10 serving as a switching device, and the primary winding 25 of the transformer 24 has a center tap connected to a variable output signal line of said variable output signal generating device 12, while a pair of the output terminals 22A and 22B are connected to both ends of the secondary winding 26 that outputs the stimulation signals, respectively. Moreover, one end of the primary winding 25 of the transformer 24 is connected to a drain of the source-grounded FET 14, while the other end of the primary winding 25 of the transformer 24 is connected to a drain of the source-grounded FET 15. The +side PWM signals from the CPU 2 are supplied to a gate that is a control terminal of the FET 14, while the −side PWM signals from the CPU 2 are supplied to a gate that is a control terminal of the FET 15.

The CPU 2 comprises, as a functional configuration of a control sequence provided in a storing device, an interval signal generating device 31 for generating an interval signal that determines on time and off time of the variable output signal; an amplifying command signal generating device 32 to generate an amplifying command signal for determining the amplitude of the variable output signal; a PWM signal generating device 33 to output a PWM signal to either one of the gates of the FETs 14 and 15; and an operating-conditions control device 35 for storing operating conditions of the variable output signal and displaying the operating conditions on a display device 11 or updating them according to need. The operating conditions mentioned here include: a first time width carried on from the start of output of the variable output signals (eventually the stimulation signals) until the gradually increasing amplitude thereof is finally stabilized; and an amplitude of the variable output signal after the first time width, in addition to the conduction period in which the on-pulses of the variable output signals are repeatedly generated and the pause period in which no on-pulse is generated.

In the present case, in synchronization with the interval signals of the on-pulses given by the interval signal generating device 31, the interval signals of the on-pulses are generated from the variable output signal device 12, and the rectangular pulse groups comprising a plurality of rectangular wave pulses are output, as PWM signals, from PWM signal generating device 33 to the FETs 14 and 15. Preferably, the rectangular wave pulse groups at this time are output alternately to either one of the FETs 14, 15 every time the variable signals of the on-pulses are generated from the variable output signal generating device 12, while the PWM signal generating device 33 generates PWM signals so that in each rectangular pulse group, the time width of each rectangular pulse gradually increases from the rising edge of each pulse group until the lapse of the first half of the conduction period and then gradually decreases as coming closer to the falling edge of each rectangular wave pulse group.

The interval signal generating device 31 is configured so as to repeatedly generate the interval signal of the on-pulse during the conduction period of the variable output signal that is preset and stored in the operating-conditions control device 35, however generates no interval signal of the on-pulse during the pause period of the variable output signal. At the same time, the amplifying command signal generating device 32 is so configured as to generate the amplifying command signal so that the amplitude of the variable output signal gradually increases from the start of the output of the variable output signals until the lapse of the first time width and then coincides with the preset amplitude thereof after the lapse of the first time width.

The switch 4 corresponds to the fourth operation device and the fifth operation device, alternately giving the CPU 2 such commands as to start or stop the output of the PWM signal, the variable output-signal, eventually the stimulation signal, every time the switch 4 is pushed. In the meantime, the first operation device for stating the output of the stimulation signal and the fifth operation device for stopping the output of the stimulation signal may be separated.

The switch 5 corresponds to the second operation device for varying the amplitude of the electric pulse output as the stimulation signal so as to make it possible to vary the amplitude of the variable output signal after the lapse of the first time width preset in the operating-conditions control device 35 every time the switch 5 is pushed.

The switch 6 corresponds to the third operation device for varying the conduction period in which the electric pulse group contained in the stimulation signal is generated so as to make it possible to change the conduction period of the variable output signal preset in the operating-conditions control device 35 every time the switch 6 is pushed.

The switch 7 corresponds to the fourth operation device for varying the pause period in which the electric pulse group contained in the stimulation signal is not generated so as to make it possible to vary the pause period of the variable output signal preset in the operating-conditions control device 35 every time the switch 7 is pushed.

The switch 8 corresponds to the fifth operation device for varying the first time width defined from the start of the output of the variable output signals, eventually the stimulation signals until the amplitude of the electric pulse group is increased to a certain level and then stabilized, so that the first time width preset in the operating-conditions control device 35 may be varied every time the switch 8 is pushed.

It should be noted that as shown in FIG. 1, the apnea preventing stimulation apparatus of the present embodiment is not provided with any respiratory-condition monitoring device for monitoring the respiratory condition of a patient. In other words, the stimulation signal generated from between the output terminals 22A, 22B of the conductor unit 21 is applied without regard to the respiratory condition of a patient.

Next, the structure of the conductor unit 21 used in this apparatus is described in more detail with reference to FIG. 2. Numerals 22A and 22B designate a pair of the output terminals mentioned above, each of which is electrically connected with the stimulus generating device 13 provided inside the main body of the apparatus (not shown) through a connecting cord 41.

Numeral 42 designates a sheet member which holds the output terminals 22A and 22B in parallel with each other. The sheet member 42 is composed of a material rich in flexibility and adhesiveness (for example, gel-like substance) so as to make it possible to be attached detachably to the mental region P of a patient. It should be particularly noted that the sheet member 42 of the present embodiment arranges the output terminals 22A and 22B in such a manner that the output terminals 22A and 22B may be arranged on the front and rear sides of the mental region P of a patient, respectively. That is, if each electrode of the conductor unit 21 is arranged on right and left sides of the mental region P, due to the influence of the stimulation signal applied to the electrodes, brain waves cannot be detected correctly when detecting the sleeping condition of a patient with brain waves, using the apparatus of the present embodiment. According to the present embodiment, however, the output terminals 22A and 22B are arranged on the front and rear sides of the mental region P after the sheet member 42 is stuck on the mental region P of the patient, and thus the influence of the stimulation signal on the brain waves can be reduced to the minimum, enabling it to be discerned correctly by an electroencephalograph whether the patient is in an asleep condition or not.

Figure 3:
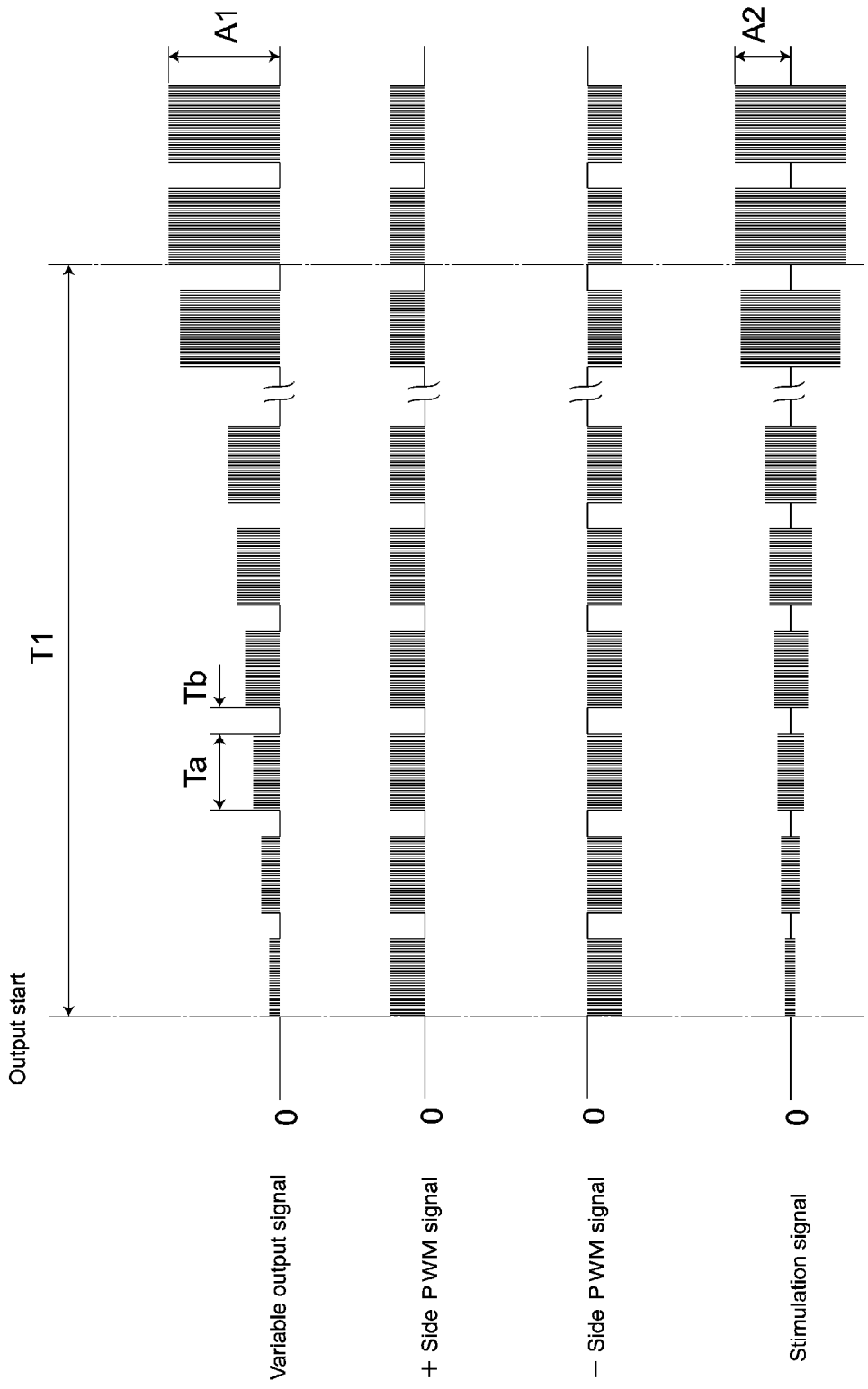
FIG. 3 is a waveform diagram of a stimulating signal showing waveforms in respective parts thereof from the start of output until elapse of a first time width in accordance with the first embodiment of the invention.
Figure 4:
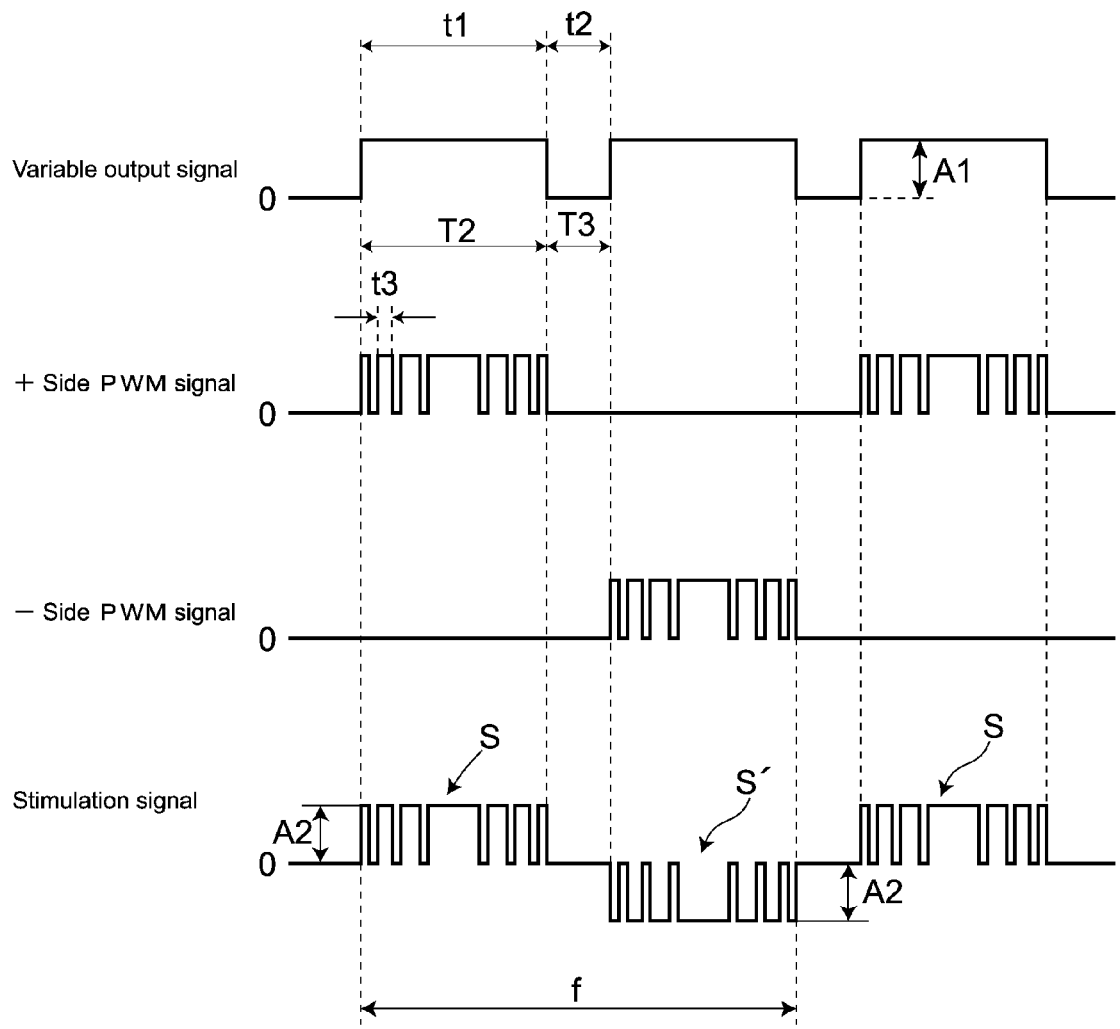
FIG. 4 is an enlarged waveform diagram of the stimulating signal showing waveforms in respective parts thereof on the way to the lapse of the first time width in accordance with the first embodiment of the invention.
Figure 5:
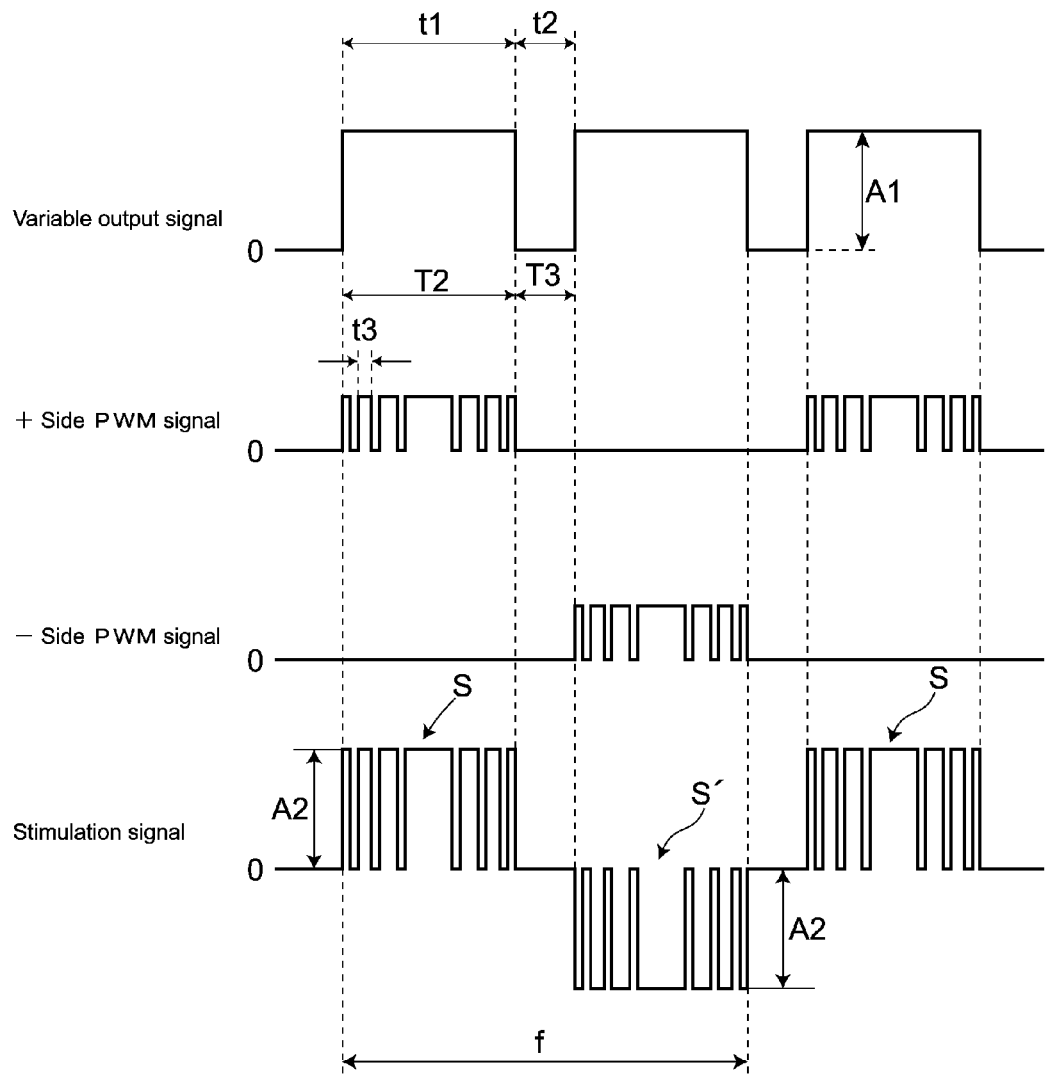
FIG. 5 is an enlarged waveform diagram of the stimulating signal showing waveforms in respective parts thereof after the lapse of the first time width in accordance with the first embodiment of the invention.

Next, the behavior of the above-configured apparatus is described with reference to waveform diagrams shown in FIGS. 3 to 5. In each figure, the uppermost waveform shows a variable output signal from the variable output signal generating device 12, followed by voltage waveforms of +side PWM signals, −side PWM signals and stimulation signals across the output electrodes 22A, 22B. FIG. 3 shows each waveform generated in respective parts during the time elapsed from the start of the output of the stimulating signal to the end of the first time width T1. FIG. 4 shows the waveforms in respective parts thereof on the way to the end of the first time width, while FIG. 5 shows waveforms in respective parts thereof after the end of the first time width, respectively.

Figure 2:
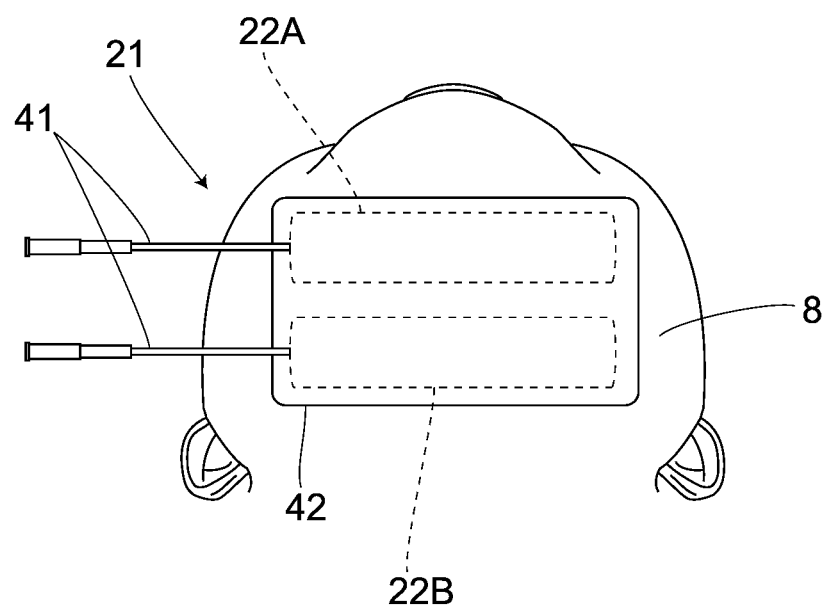
FIG. 2 is an explanatory diagram showing conductor elements attached to a mental region of a patient in accordance with the first embodiment of the invention.

When using the apparatus of the present invention, the conductor unit 2 is attached in advance to the mental region P of a patient, utilizing the adhesiveness of the sheet member 42, as shown in FIG. 2. Since the sheet member 42 is formed in an oblong shape in order for an operator to be given an proper orientation in attaching the conductor unit 21, the longer side of the sheet member 42 is inevitably attachable to the horizontal direction of the mental region P, thus juxtaposing the output terminals 22A and 22B on the front and rear sides of the mental region P.

Next, when the switch 4 is pushed to direct the start of output of the stimulation signal, the variable output signals of a plurality of on-pulses are generated during predetermined on time t1 and off time t2 (see FIG. 4) during the conduction period Ta shown in FIG. 3, and then during the subsequent pause period Tb, the interval signals generating no variable output signal of on-pulses are repeatedly given to the output pulse generating section 17 of the variable output signal generating device 12 from the interval signal generating device 31. At the same time, the amplifying command signal for gradually increasing the amplitude A1 of the variable output signal until the lapse of the first time width T1 (see FIG. 3) stored in the operating-conditions control device 35 is given to the amplitude setting section 18 of the variable output signal generating device 12 from the interval signal generating device 31. As a result, during the first time width T1 from the start of the output of the stimulation signal until the lapse thereof, the variable output signal with the preset ON time t1 and OFF time t2 with the amplitude A1 thereof increased gradually, is output from the variable output signal generating device 18 to the center tap of the primary winding 25 of the transformer 24 during the conduction period Ta, while in reaching the pause period Tb, such variable output signal is no longer applied to the center tap of the primary winding 25 of the transformer 24.

On the other hand, during the ON-time t1 in which the variable output signal of the on pulse is output from the variable output signal generating device 18, the PWM signal generating device 33 outputs rectangular pulse groups comprising a plurality of the rectangular pulses alternately to either of the gates of the FETs 14, 15 as the PWM signal. At this time, each of the rectangular pulses has higher-frequency components than those of the on pulse of the variable output signal. However, until half the time width T2 (=ON time t1) in which the rectangular pulse group is output has elapsed from the rising edge of the rectangular pulse group, each rectangular pulse time width t3 gradually widens and subsequently as coming closer to the falling edge of the rectangular pulse group, each rectangular pulse time width t3 gradually narrows.

Then, when the rectangular pulse group is supplied from the PWM signal generating device 33 of the CPU 2 to the FET 14 as the +PWM signal with the variable output signal of the on pulse being output to the center tap of the primary winding 25 of the transformer 24, the FET 14 is turned on while each rectangular pulse is being output, so that one end (a dotted side) of the primary winding 25 gets earthed to induce a voltage at one end (a dotted side) of a secondary winding 26. Further, similarly when the rectangular pulse group is supplied from the PWM signal generating device 33 of the CPU 2 to the FET 15 as the −PWM signal with the variable output signal in the form of the on pulse being output to the center tap of the primary winding 25 of the transformer 24, the FET 15 is turned on while each rectangular pulse is being output, so that the other end (an undotted side) of the primary winding 25 gets earthed to induce a voltage at the other end (an undotted side) of a secondary winding 26. Consequently, as shown in FIGS. 3, 4, during the conduction period Ta, every time the variable output signal in the form of the on pulse is output from the variable output signal generating device 12, the stimulation signals in which a positive electric pulse group S comprising a plurality of the electric pulses and a negative electric pulse group S' comprising a plurality of the electric pulses are alternately generated with an off period T3 interposed therebetween are applied iteratively across the output terminals 22A, 22B.

Further, the amplitude A2 of electric pulse groups S, S' is proportional to the amplitude A1 of the variable output signal. Therefore, immediately after the output start of the stimulation signals, i.e., shortly after falling edge asleep, the amplitude A2 of the electric pulse groups S, S' constituting the stimulation signals is so small as to be hardly perceptible, while as time goes by for the patient to fall asleep, the amplitude A2 of each of electric pulse groups S, S' increases to a level suitable for the therapy.

In addition, since the time taken to fall asleep varies greatly from individual to individual, it is preferable that the time width T1 required for the electric pulse groups, S, S' to increase to the level suitable for therapy from the output start of the stimulation signals can be arbitrarily varied by an external operation. In the present embodiment, the time width T1 can be varied ranging from e.g., 0 to 30 minutes by pushing the switch 8 that is the operation device.

As another modified example, without fixing a rate of increase in the amplitude A2 of each of the electric pulse groups S, S' during the time width T1, the rate of the increase may be increased over time. Thus, for a short period from the output start of the stimulation signals, the amplitude A2 of each of the electric pulse groups S, S' is increased moderately, so that the patient is less disturbed by the stimulation signals to be able to fall asleep.

According to the present embodiment, the amplitude A2 of each electric pulse within the same electric pulse groups S, S' is constant and increases gradually as time elapses with each of the electric pulse groups S, S' defined as a basic unit. The amplitude A2 of each of the electric pulses, however, may be increased gradually with each electric pulse defined as the basic unit.

When a predetermined time width T1 has elapsed, the amplitude A1 of the variable output signal approaches the amplitude of the variable output signal that is stored in the operating conditions control device 35 and is subsequent to the lapse of the first time width, and then the amplitude A2 of the electric pulse constituting the stimulation signals is also stabilized and reaches a nearly constant value. During this period of time, the stimulation signals that can rapidly prevent an upper-airway obstruction is applied constantly from the output terminals 22A, 22B to the mental region P of the patient irrespective of the respiratory condition of the patient. Consequently, no device for monitoring the respiratory condition is required as was conventionally needed and no stimulation signal occurs abruptly in synchronization with the occurrence of the sleep apnea. Hence, the patient can enjoy feeling of sound sleep.

Also, after the predetermined time width T1 has elapsed, every time the variable output signal in the form of the on pulse is output from the variable output signal generating device 12 during the conduction period Ta, the PWM signal generating device 33 of the CPU 2 outputs the rectangular pulse group comprising a plurality of the rectangular pulses alternately to either of the gates of the FETs 14, 15 as the PWM signal. Thus, every time the variable output signal in the form of the on pulse is output from the variable output signal generating device 12, the positive electric pulse group S comprising a plurality of the electric pulses and the negative electric pulse group S' comprising the plurality of the electric pulses are alternately generated across the output terminals 22A, 22B with the off period T3 interposed therebetween to be applied to the mental region P of the patient as the stimulation signals.

Moreover, during the time elapsing from the rising edge of the rectangular pulse group to half the time width T2 in which the rectangular pulse group is output, the time width t3 of each rectangular pulse gradually widens, and subsequently as coming closer to the falling edge of the rectangular pulse group, the time width t3 of each rectangular pulse gradually narrows. As a result, the stimulation signals are generated across the terminals 22A, 22B in such a manner that during the time elapsing from the rising edge of the electric pulse groups S, S' to half the time width T2 in which the electric pulses S, S' are output, the time width t3 of each electric pulse gradually widens, and subsequently as coming closer to the falling edge of the electric pulses S, S', the time width t3 of each electric pulse gradually narrows. When the stimulation signals comprising such electric pulse groups S, S' are applied to the patient (a human body), the higher the frequency of the signal component, the lower the impedance of the human body since the human body behaves like a capacitive element such as a capacitor, so that the overall waveform of each of the electric pulse groups S, S' is distorted within the human body to form a waveform approximate to a low-frequency sinusoidal waveform. Consequently, extremely soft feeling of stimulation can be obtained as compared with the feeling obtained by a rectangular waveform with the same current and frequency. Besides, in the stimulation signals, high-frequency components obtained by the switching operations of the FETs 14, 15 remain and therefore therapeutic effects by the high-frequency components hold promise.

Additionally, if the patient becomes awake during the therapy, then, by pushing the switch 4 to direct stoppage of outputting the stimulation signals, the variable output signal from the variable signal generating device 12 and the PWM signal from the PWM signal generating device 33 quickly stop their outputs to immediately cut off the outputs of the stimulation signals to the mental region P. As a result, the patient can get relief from uncomfortable feeling resulting from uninterrupted application of the stimulation signals at the time of awakening. Further, when getting back sleeping subsequently, only pushing the switch 4 again enables the CPU 2 to be directed to start outputting the stimulation signals and besides as no strong stimulation signal is applied directly after falling asleep, the adverse influence on sleep resulting from the stimulation signals can be eliminated.

As a preferred example of the present invention, a recurrent frequency f of the positive and negative electric pulse groups S, S' shown in FIGS. 4, 5 is 2.7 kHz, and the conduction period Ta of the variable output signal, eventually of the stimulation signal, is 30 sec., and the pause period Tb is 10 sec. Whilst a rate of suffering the apnea varies greatly between individuals, it is preferable that the aforementioned frequency f, the conduction period Ta, and the pause period Tb may be variable arbitrarily by the external operation.

Practically, in the present embodiment, by pushing the switch 6 serving as the third operation device, the conduction period Ta of the stimulation signal in which the electric pulse groups S, S' are intermittently generated is readily variable. Further, by pushing another switch 7 serving as the fourth operation device, the pause period Tb of the stimulation signals in which no electric pulse groups S, S' are generated is readily variable.

Furthermore, according to the present embodiment, by pushing the switch 5 serving as the second operation device, input and output gains of the amplitude setting section 18 are changed, so that the amplitude A1 of the variable output signal, eventually the amplitude A2 of each electric signal constituting the stimulation signals is wholly increased or decreased. Thus, if, for example, the stimulation signals are so strong as to cause awakening during sleep, the stimulation signals are adjusted by the switch 5 to decrease the amplitude A2, whereas if no sufficient therapeutic effects can be obtained to the apnea during sleep, the switch 5 can adjust the amplitude A2 to increase the amplitude A2.

Besides, though not shown, if the on period T2 and off period T3 of the electric pulse groups S, S' are made arbitrarily variable by an external operation device, more effective therapeutic effects can be obtained. In addition, this can be simply realized only by changing a control program inside the CPU 2.

Figure 6:
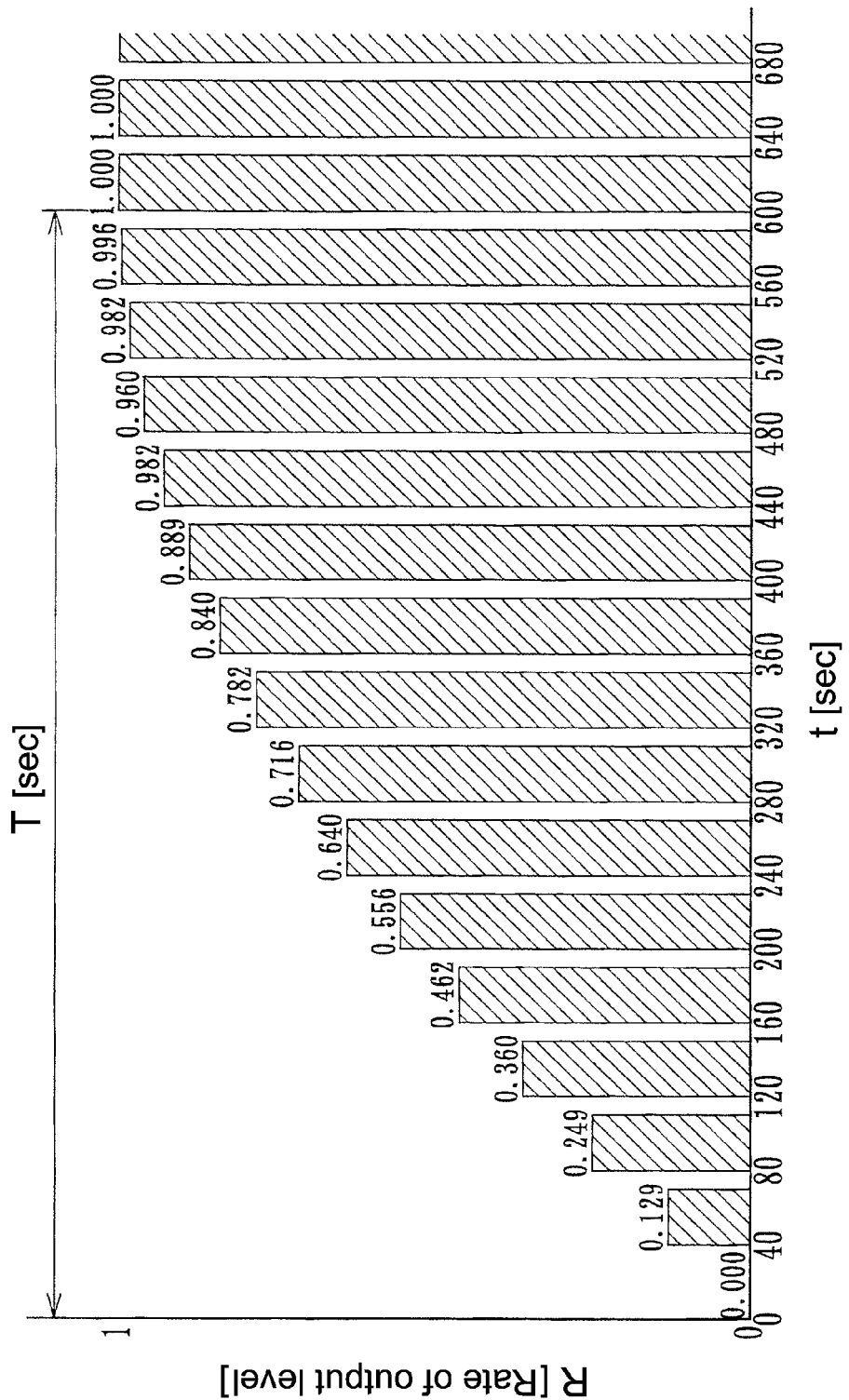
FIG. 6 is a graph showing rate of output level R of amplitude of an electric pulse ranging from a start of output of the stimulation signal to an end of a first time width in accordance with the first embodiment of the invention.

FIG. 6 shows, by way of a graph, a preferred example of rates of output levels R of the amplitudes in the electric pulse groups S, S' during the time width T1. In FIG. 6, the abscissa axis denotes time t from the start of the output of the stimulation signal, while the ordinate axis denotes a rate of output level R of the amplitudes A2 in the electric pulse groups S, S'. Besides, T (=600 sec) corresponds to the time width T1 described above. This time width T, however, is changeable by pushing the switch 8.

In the preferred example, the rate of output level R of the amplitudes A2 is calculated based on the following formula.

$$R = 1 - ((1 - t/T))^N$$

where $1.5 \leq N \leq 3$

The amplifying command signal generating device 32 transmits an amplifying command signal to the variable output signal device 12 so that the stimulation signal is generated from the stimulation generating device 13 until the time t from the start of the output of the stimulation signal reaches the end of the time width T. Thereafter, when the time t from the start of the output of the stimulation signal has reached the end of the time width T, the amplitude A2 of the electric pulse groups S, S' reaches 1 to be stabilized.

FIG. 6 shows the relationship between the time t and the amplitudes A2 where n=2. When N is set at a numeral between 1.5 and 3, immediately after the start of the output of the stimulation signals, the amplitudes A2 of the electric pulse groups S, S' do not increase abruptly to permit a patient to be less affected by the stimulation signals. Further, when N is set at a numeral between 1.5 and 3, the rate of output level R of the amplitude A2 in the electric pulse groups S, S' does not reach 1 until just before the time t from the output start of the stimulation signal reaches the end of the time width T, thus permitting the emotional strain on the patient to be eased.

In addition, in the graph in FIG. 6, the rate of output level R of the amplitudes A2 in the electric pulse groups S, S' is increased in a stepwise fashion every certain length of time (40 sec). The rate of output level R, however, may be continuously increased as the time t progresses. Further, there may be separately provided an operation device for enabling a set value of the N to be variable.

According to the present embodiment as described above, there is provided the apnea preventing stimulation apparatus in which the conductive unit 21 is attached to the mental region P of the patient and the electric pulses conduct from the conductive unit 21 to the mental region P of the patient to thus apply stimuli thereto. The apnea preventing stimulation apparatus includes the switch 4 serving as the first operation device for starting to output the stimulation signals, and the stimulation generating device 13 for outputting, across the output terminals 22A, 22B, the stimulation signals that repeat alternately, for a predetermined period of time, the conduction period Ta during which the electric pulse groups S, S' comprising a plurality of the electric pulses are generated and the pause period Tb during which no electric pulse groups S, S' are generated by operating the switch 4. Further, the stimulation generating device 13 outputs the stimulation signals where the amplitude A2 of the electric pulse gradually increases during the elapse of the first time width from the start of the output of the electric pulse so that the amplitude A2 of the electric pulse is small immediately after the start of the output of the stimulation signal and subsequently increases as the patient falls asleep with time.

In this case, the stimulation signals that alternately repeat the conduction period Ta during which the electric pulse groups S, S' are generated from the stimulation generating device 13 via the conductive unit 21 and the pause period Tb during which no electric pulse groups S, S' are generated are effectively applied to the mental region P of the patient. Consequently, even if not bothering to monitor the respiratory condition during sleep, the upper-airway obstruction can be quickly avoided. Further, the stimulation signals that repeat alternately the conduction period Ta of the electric pulse groups S, S' applied to the patient and the pause period Tb thereof are applied irrespective of the presence or absence of the respiration of the patient, the patient doesn't become awake by sensing the stimulation signals, resulting in sound sleep of the patient. Therefore, without monitoring the respiratory condition, the sleep of the patient becomes undisturbed as much as possible to thus enable the stimulation signals to be effectively applied to the mental region P of the patient.

Alternatively, whilst in the present embodiment, the electric pulse groups S, S' are schemed to be generated at intervals of the off period T3, the stimulation signals, however, may be schemed to generate the electric pulse groups S, S' continuously without interposing the off period T3.

Further, in the present embodiment, there is provided the switch 5 serving as the second operation device that can vary the amplitude A2 of the electric pulse contained in the stimulation signals. Thus, the amplitude A2 of the electric pulse generated during the conduction period Ta can be varied arbitrarily by the switch 5. Hence, the electric pulse of the optimal amplitude A2 can be applied to any patients.

Furthermore, according to the present embodiment, there is provided the switch 6 serving as a third operation device that can vary the conduction period Ta. Thus, the conduction period Ta during which the electric pulse groups S, S' are generated can be varied arbitrarily by the switch 6. As a result, the stimulation signals with the optimal conduction period Ta can be applied to any patients.

Moreover, in the present embodiment, there is provided the switch 7 serving as a fourth operation device that can vary the pause period Tb. Thus, the pause period Tb where no electric pulse groups are generated can be arbitrarily varied by the switch 7. As a result, the stimulation signals with the optimal pause period Tb can be applied to any patients.

Besides, according to the present embodiment, there is provided the common switch 4 serving as the fifth operation device for stopping outputting the stimulation signals. In this case, when a patient awakes from any cause, the therapy can be stopped temporarily by re-operating the switch 4 to stop outputting the stimulation signals. In this fashion, the switch 4 thus provided enables an output start and an output stop to be selected freely by the patient according to the patient's own will. Additionally, the above switches 4 to 7 are not limited to a momentary type.

Further, in the present embodiment, the stimulation signal generating device 13 outputs the stimulation signals in which a ratio at which the amplitude A2 of the electric pulse is increased is not made constant but is increased with time, during the first time width T1 in which the amplitude A2 of the electric pulse groups rises from the start of the output of the stimulation signal to a certain level to be stabilized.

Thus, during the first time width T1 in which the amplitude A2 of the electric pulse groups rises from the start of the output of the stimulation signal to a certain level to be stabilized, the ratio at which the amplitude A2 of the electric pulse is increased is not made constant but is increased with time. As a result, the amplitude A2 of the electric pulse is less increased for a while from the and the patient is less disturbed by the stimulation signals and can fall asleep.

Further, as shown in FIG. 6, the rate of output level R of the amplitude A2 in the electric pulse during the elapse of the first rime width T is increased by utilizing the above formula. As a result, the amplitude A2 of electric pulse groups S, S abruptly increase immediately after the start of the output of the stimulation signal. thus allowing the patient to be less affected by the stimulation signals. Until just before the time t reaches the end of the time width T from the start of the output of the stimulation signal, the rate of output level R of the amplitude A2 in electric pulse groups S, S does not reach 1, permitting an emotional strain on the patient to be eased.

Furthermore, according to the present embodiment, there is provided the switch 8 serving as a sixth operation device that varies the first time width T1. In this case, since the time required for getting to sleep varies between individuals, if the first time width T1 can be varied by the switch 8, the stimulation signals that can prevent surely the apnea can be applied to any patients when the patient has fallen asleep. In addition, also it goes without saying that the switch 8 is not limited to the momentary type.

Moreover, according to the present embodiment, there is provided the stimulation generating device 13 for outputting the stimulation signals in which a time width t3 of the plurality of the electric pulses constituting the electric pulse groups S, S' is varied during an output period of the electric pulse groups S, S'.

Thus, since the stimulation generating device 13 varies arbitrarily the time width t3 of each electric pulse constituting the electric pulse groups S, S', low-frequency waveforms entering the patient can be distorted into desirable shapes depending on variations in the time width t3 of the electric pulse.

Furthermore, according to the present embodiment, the stimulation generating device 13 generates alternately the positive and negative electric pulse groups S, S' with the second time width T2 during the conduction period Ta. Thus, the positive and negative electric pulses S, S' are alternately applied successively to the mental region P of the patient during the conduction period Ta to thereby be able to avoid the apnea reliably.

Moreover, according to the present embodiment, the stimulation generating device 13 outputs the stimulation signals in such a way that during the time elapsing from the rising edge of the electric pulses S, S' to half the second time width T2, the time width t3 of each electric pulse gradually widens and subsequently as coming closer to the falling edge of the electric pulses S, S', the time width t3 of each electric pulse gradually narrows.

Thus, the stimulation generating device 13 outputs the stimulation signals in such a way that the positive and negative electric pulse groups S, S' that comprise the plurality of the electric pulses and have the second time width T2 as a whole is generated periodically, and during the time elapsing from the rising edge of the electric pulse groups S, S' to half the second time width T2, the time width t3 of each electric pulse gradually widens and subsequently as coming closer to the falling edge of the electric pulse groups S, S', the time width t3 of each electric pulse gradually narrows. As a result, irrespective of recurrence of the electric pulse groups S, S' containing a plurality of high-frequency signal components (electric pulses) applied from the conductive unit 21 to the patient as the stimulation signals, each of the electric pulse groups S, S' is distorted by capacitive effects of the patient, so that the stimulation signals are transformed into the waveforms approximate to the low-frequency sinusoidal waveforms. Consequently, the apnea can be effectively avoided while giving extremely soft feeling of stimulation as compared to the feeling caused by a rectangular waveform with the same current and frequency.

Further, according to the present embodiment, the conductive unit 21 comprises the output terminals 22A, 22B serving as a couple of the electrodes to which the stimulation signals are applied and the adhesive sheet member 42 that holds these output terminals 22A, 22B and is detachable to the mental region P of the patient.

Thus, only sticking the adhesive sheet 42 to the mental region P of the patient enables the conductive unit 21 containing the output terminals 22A, 22B to be mounted on a desired portion. As a result, a troublesome labor for mounting a couple of the output terminals 22A, 22B can be saved.

Besides, the pair of the output terminals 22A, 22B in which the sheet member 42 is formed long from side to side is arranged so that the couple of the output terminals 22A, 22B are juxtaposed in the front and back direction of the mental region P of the patient. As a result, only adhering the sheet member 42 to the mental region P of the patient enables the couple of the output terminals 22A, 22B to be juxtaposed in the direction of the mental region P of the patient. Hence, the influence on the brain wave by the stimulation signals can be restrained to a maximum extent, so that it can be precisely checked out whether the patient is asleep or not.

Figure 7:
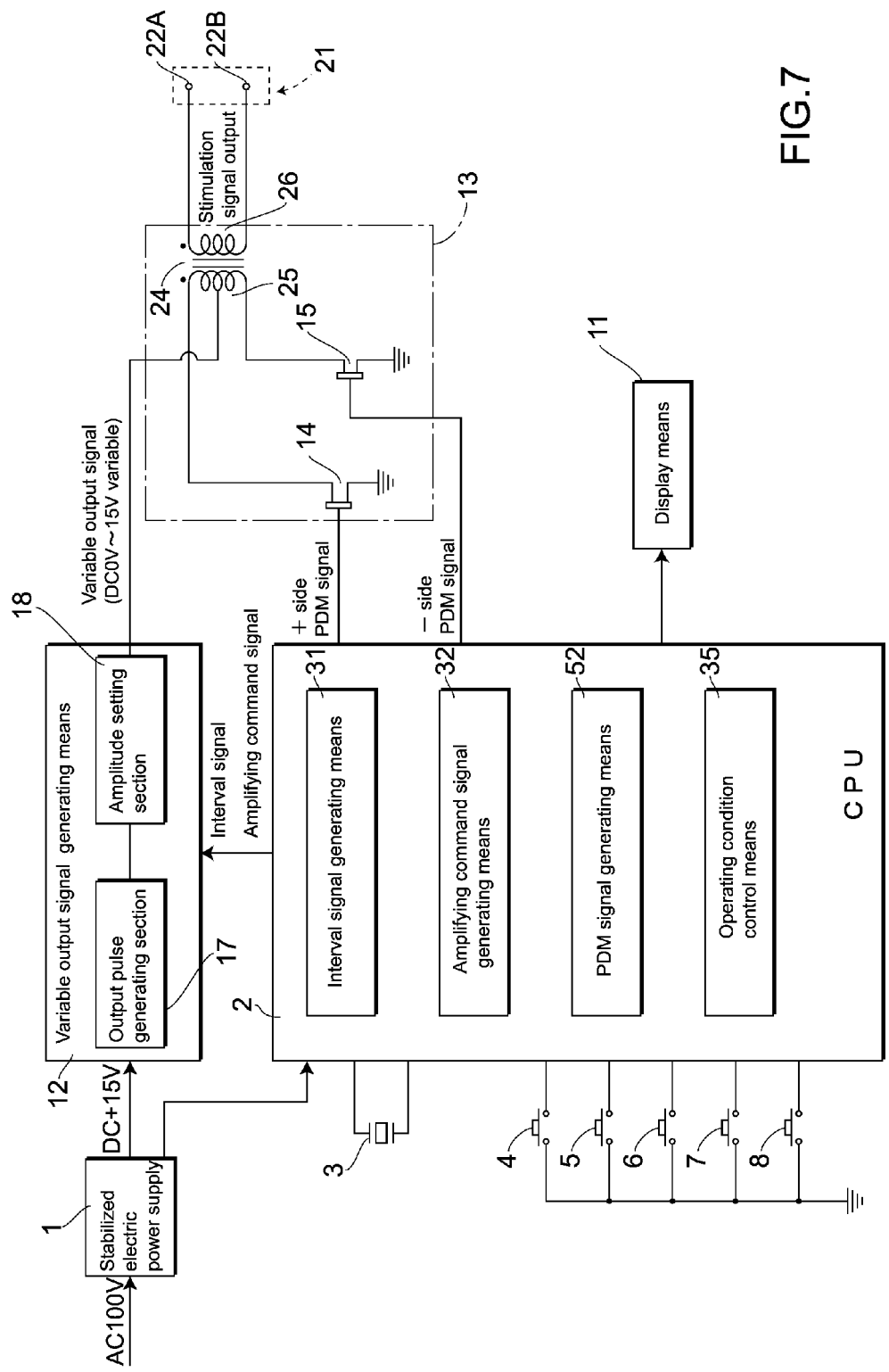
FIG. 7 is a block diagram showing an overall structure of an apnea preventing stimulation apparatus in accordance with a second embodiment of the invention.
Figure 8:
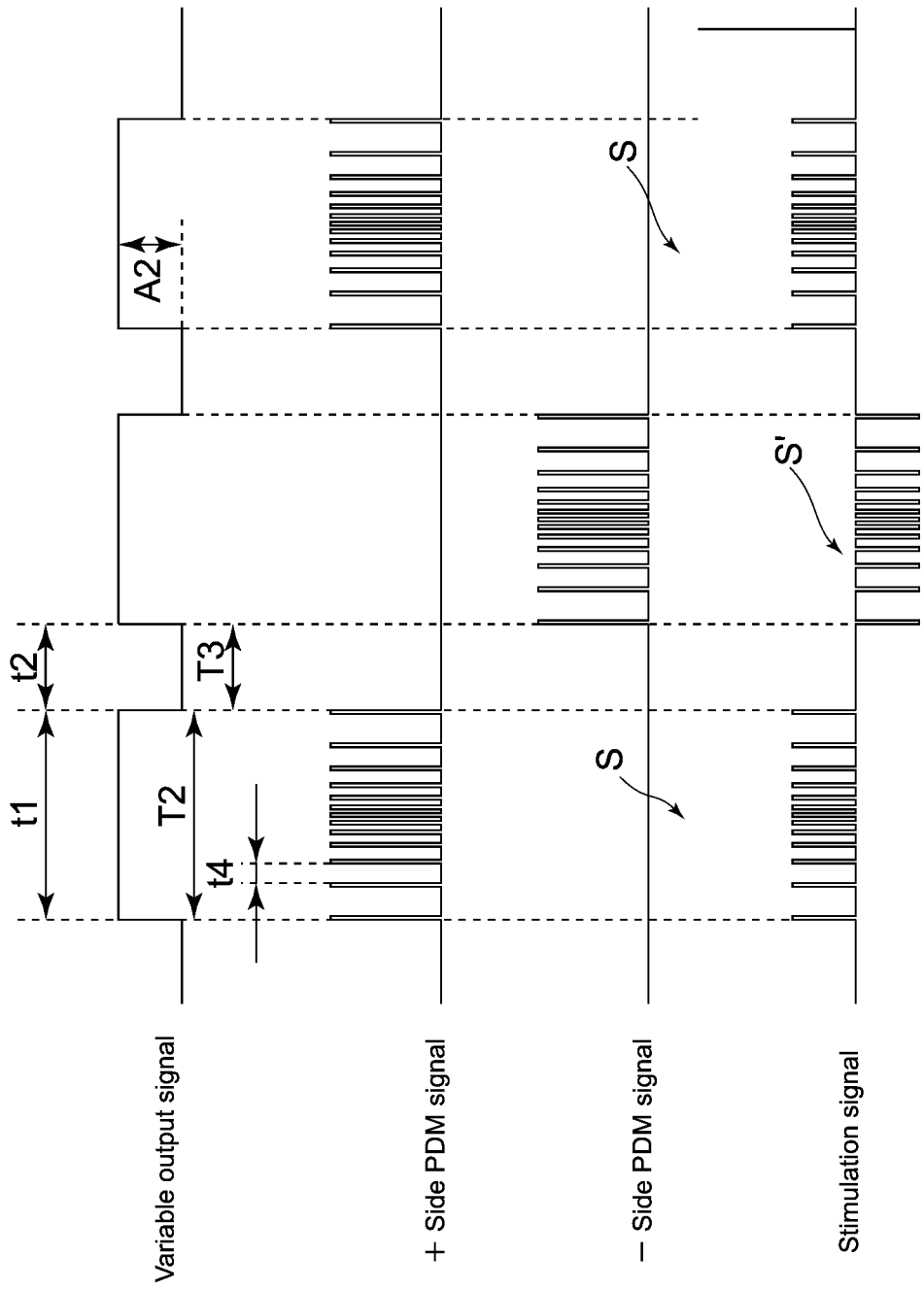
FIG. 8 is an enlarged waveform diagram of the stimulating signal showing waveforms in respective parts thereof on the way to the lapse of the first time width in accordance with the second embodiment of the invention.

Next is a description of a second embodiment of the present invention with reference to FIG. 7 to FIG. 9. Additionally, the same numeral symbols are used for parts the same as in the first embodiment and descriptions for common parts are omitted to avoid overlap as much as possible.

In FIG. 7 showing an overall system of an apparatus, the present embodiment replaces the PWM signal generating device 33 in the first embodiment with a PDM (Pulse Density Modulation) signal generating device 52 for outputting a PDM signal to either of the gates of the FETs 14, 15. The PDM signal generating device 52 outputs rectangular pulse groups comprising a plurality of rectangular wave pulses to the FETs 14, 15 as the PDM signal in synchronization with interval signals in the form of the on pulse generated by the interval signal generating device 31. The rectangular pulse groups at this time are preferably output alternately to either of the FETs 14, 15 every time the interval signal in the form of the on pulse is generated from the variable output signal generating device 12. Besides, in each of the rectangular pulse groups, each rectangular pulse is generated in such a way that time intervals (off time intervals) between adjacent rectangular pulses narrow gradually to increase pulse density per unit time during the time elapsing from the rising edge of the rectangular pulse group to half the conduction period, and subsequently as coming closer to the falling edge of the rectangular pulse group, the time intervals between adjacent rectangular pulses widen gradually to decrease the pulse density per unit time. Each of the rectangular pulses in this case has a constant on time width. In addition, the remaining parts of the apparatus are in common with those of the first embodiment.

Next is a description of the performance of the aforementioned apparatus based on waveform diagrams in FIGS. 8, 9.

In addition, FIG. 8 shows waveforms of each part in mid-course of the first time width T1, while FIG. 9 shows waveforms of each part after the first time width T1 has elapsed.

As described in the first embodiment, when the apparatus is used, firstly, the conductive unit 21 is mounted on the mental region P of the patient using the sheet member 42 and then the stimulation signals are directed to start outputting by pushing the switch 4. Also in this case, immediately after the stimulation signals has started to output, i.e., immediately after falling edge asleep, the amplitude A2 of the electric pulse groups S, S' constituting the stimulation signals is so small as to be hardly felt by the patient. Afterward, as the time advances for the patient to get to sleep, the amplitude A2 of the electric pulse groups S, S' is increased up to a level suitable for therapy. Then, when a predetermined time width T1 has elapsed, the stimulation signals, capable of avoiding quickly the upper-airway obstruction, are get applied continually to the mental region P of the patient from the output terminals 22A, 22B irrespective of the respiratory condition of the patient.

In a series of these performances, according to the present embodiment, every time the variable output signal in the form of the on pulse is output from the variable output signal generating device 12 during the conduction period Ta, the PDM signal generating device 33 of the CPU 2 outputs the rectangular pulse groups comprising a plurality of rectangular wave pulses alternately to either of the gates of the FETs 14, 15 as the PDM signal. Therefore, every time the variable output signal in the form of the on pulse is output from the variable output signal generating device 12, a positive electric pulse group S comprising a plurality of the electric pulses and a negative electric pulse group S' comprising a plurality of the electric pulses are generated alternately across the output terminals 22A, 22B with the off period T3 interposed therebetween, so that these pulses are applied to the mental region P of the patient as the stimulation signals.

Further, during the time elapsing from the rising edge of the rectangular pulse group to half the time width T2 where the rectangular pulse group is generated, the off time width t4 between each of rectangular pulses gradually narrows to increase the pulse density thereof, and subsequently as coming closer to the falling edge of the rectangular pulse group, the off time width t4 between each of the rectangular pulses widens gradually to decrease the pulse density thereof. Thus, the stimulation signals are generated. Then, these stimulation signals conduct via the conductive unit 21 to the mental region P of the patient (a human body) that behaves like a capacitive element such as a capacitor.

In this case, in a portion where the off time widths t4 between the electric pulses constituting the stimulation signals are wider, i.e., an electric pulse frequency is lower, a charge-discharge amount for an equivalent electrostatic capacity of the human body is little, so that variations in a voltage waveform between the terminals 22A, 22B becomes moderate. Adversely, in a portion where the off time widths t4 between the electric pulses constituting the stimulation signals are narrow, i.e., the electric pulse frequency is higher, the charge-discharge amount for the equivalent electrostatic capacity of the human body is large, so that the variations in a voltage waveform between the terminals 22A, 22B becomes sharp. As a result, within the human body, the stimulation signals are modulated by a low-frequency signal approximate to a sinusoidal wave to form a waveform in which high-frequency rectangular wave signals are superimposed on the low-frequency signal. The low-frequency signal thus distorted into a sinusoidal shape can cause an extremely soft feeling of stimulation as compared to feeling caused by the rectangular wave with the same current and frequency. Besides, the high-frequency rectangular wave signals that are obtained by switching of the FETs 14, 15 are superimposed on the stimulation signals, so that the high-frequency components can be expected to cause a therapeutic gain.

Further, the on time width of each electric pulse is constant and the pause period (the off time width t4) between the electric pulses varies by the stimulation generating device 13, so that no wider electric pulse generated by the PWM modulation exists. Therefore, the charging current is supplied little by little to the equivalent electrostatic capacity of the human body to raise its charged amount (a conduction amount) moderately. Accordingly, high-frequency electric pulse components can give soft feeling of stimulation.

It is desirable to configure the stimulation generating device 13 so that in order to turn a waveform at the time of conducting to the human body into the low-frequency component approximate to the sinusoidal wave, the positive and negative electric pulse groups S, S' that comprise a plurality of the electric pulses and each have the time width T2 as a whole may be generated alternately. Besides, until half the time width T2 of the electric pulse groups S, S' elapses from the rising edge of the electric pulse groups S, S', the density of each of the electric pulses becomes gradually higher, i.e., the off time widths t4 between each of the electric pulses become gradually narrower, and subsequently as coming closer to the falling edge of the electric pulse groups S, S', the density of each of the electric pulses becomes gradually lower, i.e., the off time widths t4 between each of the electric pulses become gradually wider. Note, however, that if a time interval varying device for enabling the off time width t4 to be varied at random is added to, e.g., the control sequence of the CPU 2 instead of the aforementioned stimulation generating device 13, not only the sinusoidal wave but a triangle wave and various distorted waves can be applied to the human body, so that a unique feeling of stimulation that is different from that given by the sinusoidal wave can be obtained.

According to the present embodiment as described above, during the output period of the electric pulse groups S, S', the stimulation generating device 13 is schemed so as to output the stimulation signals in which the density of a plurality of the electric pulses that constitutes the electric pulse groups S, S' is varied. In this case, since the stimulation generating device 13 varies arbitrarily the density of the plurality of the electric pulses that constitutes the electric pulse groups S, S', the low-frequency waveform entering the patient can be distorted in a desirable state depending on the variation in the density of the electric pulses. Besides, during the output period of the electric pulse groups S, S', the time width of each electric pulse is constant and the pause period (the off time interval t4) between the electric pulses is varied by the stimulation generating device 13. Hence, by just much of absence of the electric pulse with a wider width, the charging current for the equivalent electrostatic capacity of the patient is supplied little by little to raise the charged capacity moderately, thus enabling softer feeling of stimulation to be obtained.

Further, specifically according to the present embodiment, the stimulus generating device 13 outputs the stimulation signals in such a way that during the conduction period Ta, the positive and negative electric pulse groups S, S' each having the second time width T2 are generated alternately, while until half the second time width T2 elapses from the rising edge of the electric pulse groups S, S', the electric pulse density becomes gradually higher, and subsequently as coming closer to the falling edge of the electric pulse groups S, S', the electric pulse density becomes gradually lower. When the stimulation generating device 13 outputs the stimulation signals like this, the waveform of each of the electric pulse groups S, S' is distorted within the human body, so that the stimulation signals are transformed into waveforms in which high-frequency electric pulses are superimposed on the signals approximate to the low-frequency sinusoidal waves. Consequently, the apnea can be effectively avoided while giving the extremely soft feeling of the stimulation as compared with the feeling caused by the rectangular wave with the same current and frequency.

The present invention is not limited to the aforementioned embodiments and various modifications are possible within the gist of the scope of the invention. The stimulation generating device for outputting the desired stimulation signals to the conductive unit, e.g., may be configured by the other device than the transformer and the switching device as shown in the present embodiments. Further, as a control sequence of the CPU 2, the function of the variable signal generating device 12 shown in FIG. 1 may be incorporated therein. Further, the on time and off time of each electric pulse may be set so as to form the stimulation signals into the triangle waves and a variety of distorted waveforms by utilizing the capacitive behavior of the human body, while during the conduction period of the stimulation signals the electric pulses may be generated at random. Moreover, the electric pulse groups S, S' may comprise waveforms other than those of a PWM signal and PDM signal.

What is claimed is:

1. An apnea preventing stimulation apparatus for applying a stimulus to a patient by a conductor unit for allowing electric pulses to flow from the conductor unit through a mental region of the patient, comprising:
    a first operation device for starting output of said stimulation signals; and
    a stimulus generating device for outputting stimulation signals to said conductor unit as soon as the start of output thereof is directed regardless of whether the patient is in a sleep apnea or not at that moment, said stimulation signal repeating, for a given length of time, alternately a conduction period during which an electric pulse group comprising a plurality of said electric pulses is generated and a pause period during which no said electric pulse group is generated, the plurality of said electric pulses having a constant amplitude over the conduction period in the electric pulse group,
    wherein said stimulus generating device outputs the stimulation signals in such a manner that the constant amplitude of the plurality of said electric pulses gradually increases every time said electric pulse group is output from the start of output of said stimulation signals until the lapse of a first time width, which is defined as a time width from the start of output until the gradually increasing constant amplitudes of the plurality of said electric a pulses constituting said electric pulse group repeatedly output are finally stabilized so that for a short period from the output start of the stimulation signals, the constant amplitude of said electric pulse in said electric pulse group is small and then increases as time goes by for the patient to fall asleep, and wherein when said first time width is defined as T and a time from the output start of said stimulation signals is defined as t, a rate of an output level R of the constant amplitude in the plurality of said electric pulses until the lapse of said first time width is increased according to the following formula:

$$R = 1 - ((1 - t/T))^N, \text{ where } 1.5 \leq N \leq 3.$$

2. The apnea preventing stimulation apparatus according to claim 1, further comprising a second operation device for varying amplitude of said electric pulses.

3. The apnea preventing stimulation apparatus according to claim 1, further comprising a third operation device for varying said conduction period.

4. The apnea preventing stimulation apparatus according to claim 1, further comprising a fourth operation device for varying said pause period.

5. The apnea preventing stimulation apparatus according to claim 1, further comprising a fifth operation device for stopping the output thereof.

6. The apnea preventing stimulation apparatus according to claim 1, further comprising a sixth operation device for varying said first time width.

7. The apnea preventing stimulation apparatus according to claim 1, wherein during outputs of said electric pulse group, said stimulus generating device outputs the stimulation signals in which the plurality of said electric pulses constituting the electric pulse group vary in time width.

8. The apnea preventing stimulation apparatus according to claim 7, wherein said stimulus generating device generates said electric pulse group with a second time width alternately with respect to positive and negative sides during said conduction period, and outputs stimulation signals in such a way that time width of each electric pulse gradually widens from a rising edge of said electric pulse group until half said second time width elapses, and then narrow as coming closer to a falling edge of said electric pulse group.

9. The apnea preventing stimulation apparatus according to claim 1, wherein said stimulus generating device outputs stimulation signals in which density of the plurality of said electric pulses constituting the electric pulse group varies during outputs of said electric pulse group.

10. The apnea preventing stimulation apparatus according to claim 9, wherein said stimulus generating device generates said electric pulse group with the second time width alternately with respect to positive and negative sides during said conduction period, and outputs stimulation signals in such a way that electric pulse density increases gradually from a rising edge of said electric pulse group until half said second time width elapses, and then gradually decreases as coming closer to a falling of said electric pulse group.

11. The apnea preventing stimulation apparatus according to claim 1, wherein said conductive unit comprises a couple of electrodes to which said stimulation signals are applied, and an adhesive sheet member that holds said electrodes and is detachably attached to a mental region of a patient.

12. The apnea preventing stimulation apparatus according to claim 11, wherein said sheet member arranges the electrodes so that the couple of the electrodes are juxtaposed to each other on front and rear sides of a mental region of the patient.

* * * * *